United States Patent
Kårekull et al.

(10) Patent No.: US 12,193,914 B2
(45) Date of Patent: Jan. 14, 2025

(54) HEARING PROTECTION DEVICE FOR PROTECTION IN DIFFERENT HEARING SITUATIONS, CONTROLLER FOR SUCH DEVICE, AND METHOD FOR SWITCHING SUCH DEVICE

(71) Applicant: 3M INNOVATIVE PROPERTIES COMPANY, St. Paul, MN (US)

(72) Inventors: Oscar L. Kårekull, Huskvarna (SE); Petter M. Igede, Värnamo (SE)

(73) Assignee: 3M Innovative Properties Company, St. Paul, MN (US)

( * ) Notice: Subject to any disclaimer, the term of this patent is extended or adjusted under 35 U.S.C. 154(b) by 115 days.

(21) Appl. No.: 17/756,370

(22) PCT Filed: Nov. 17, 2020

(86) PCT No.: PCT/IB2020/060827
§ 371 (c)(1),
(2) Date: May 24, 2022

(87) PCT Pub. No.: WO2021/105818
PCT Pub. Date: Jun. 3, 2021

(65) Prior Publication Data
US 2022/0387222 A1 Dec. 8, 2022

(30) Foreign Application Priority Data
Nov. 25, 2019 (EP) ................................ 19211305

(51) Int. Cl.
*H04R 1/10* (2006.01)
*A61F 11/14* (2006.01)
*H04R 5/033* (2006.01)

(52) U.S. Cl.
CPC .......... *A61F 11/145* (2022.01); *H04R 1/1041* (2013.01); *H04R 1/1083* (2013.01); *H04R 5/033* (2013.01)

(58) Field of Classification Search
CPC .... H04R 1/1083; H04R 1/1041; H04R 5/033; H04R 2460/01; H04R 25/505;
(Continued)

(56) References Cited

U.S. PATENT DOCUMENTS 5,355,418 A   10/1994  Kelsey et al.
8,649,540 B2   2/2014  Killion et al.
(Continued)

FOREIGN PATENT DOCUMENTS

DE   10114015 C2   2/2003
GB    2456296 B    2/2012

OTHER PUBLICATIONS

International Search Report for PCT International Application No. PCT/IB2020/060827, mailed on Feb. 9, 2021, 5 pages.

*Primary Examiner* — Norman Yu
(74) *Attorney, Agent, or Firm* — Katherine M. Scholz (57) ABSTRACT

The present disclosure relates to a hearing protection device 10, 10' for protection in different hearing situations A, B, C. The device 10, 10' comprises a microphone 30, 30', 32, 32', a sound reproduction unit 38 having a loudspeaker 50, 50', 52, 52' and a controller 60 for processing an ambient electrical signal. The present disclosure further relates to a controller 60 for such a hearing protection 10, 10'. The present disclosure furthermore relates to a method of switching such a hearing protection device 10, 10' in different hearing situations A, B, C.

20 Claims, 3 Drawing Sheets

(58) Field of Classification Search
CPC ............ H04R 2225/41; H04R 2430/01; H04R 2225/43; G10K 2210/1081; G10K 11/17881; G10K 11/17837; G10K 11/1783; G10K 11/17823; A61F 11/145
USPC .................... 381/56, 57, 72, 74, 58, 320, 98
See application file for complete search history.

(56) References Cited

U.S. PATENT DOCUMENTS

| | | | |
|---|---|---|---|
| 9,961,435 B1* | 5/2018 | Goyal | H04R 1/1083 |
| 2006/0140416 A1* | 6/2006 | Berg | A61F 11/12 |
| | | | 381/72 |
| 2011/0137649 A1 | 6/2011 | Rasmussen et al. | |
| 2013/0094658 A1 | 4/2013 | Holter | |
| 2016/0050476 A1* | 2/2016 | Patil | H04R 27/00 |
| | | | 715/728 |
| 2017/0142530 A1* | 5/2017 | Neumeyer | H04R 25/30 |
| 2017/0304121 A1* | 10/2017 | Rosti | H04R 3/04 |

* cited by examiner

HEARING PROTECTION DEVICE FOR PROTECTION IN DIFFERENT HEARING SITUATIONS, CONTROLLER FOR SUCH DEVICE, AND METHOD FOR SWITCHING SUCH DEVICE

CROSS REFERENCE TO RELATED APPLICATIONS

This application is a national stage filing under 35 U.S.C. 371 of PCT/IB2020/060827, filed Nov. 17, 2020, which claims the benefit of EP application Ser. No. 19/211,305.8, filed Nov. 25, 2019, the disclosure of which is incorporated by reference in its/their entirety herein.

The present disclosure relates to a hearing protection device for protection in different hearing situations as well as to a controller for such a hearing protection device. The present disclosure furthermore relates to a method of switching such a hearing protection device in different hearing situations.

Noise environments, such as worksites, airfields, helipads, and the like, may include noise sources that have the potential to damage the hearing of a person. A person operating in a noise environment may experience hearing loss from acute acoustic trauma or gradually developing noise-induced hearing loss. To help prevent hearing impairment or even total loss, a person operating in a noise environment may wear hearing protection.

Hearing protection in the form of two cups interconnected by a headband or stirrup or the like have been long employed. Hearing protection may be passive or active. Passive hearing protection may use earplugs or earmuffs that attenuate sound to a certain extent allowing for 8 hours use even when exposed up to a particular noise level, e. g. 100 dB(A). Active hearing protection may use earmuffs or earplugs that permit certain types of noise to pass through to a person by electronically or mechanically filtering out particular parts of the surrounding sound, i. e. level dependent function. For example, hearing protection systems have also been developed which include electronic amplification, attenuation and/or other signal processing of the ambient sound. Reception of ambient sound is effected by means of microphones and the sound may be amplified or damped, respectively, by electronic means before being transmitted to the wearer of the headset via loudspeakers.

In a working environment at a steadily increasing tempo, the demands on protective equipment and the like have been raised. For example, it is important that the hearing protection be employed in the correct manner, such that safety is not impaired. However, improvements to safety must not be put into effect at the expense of user friendliness and/or comfort.

For example, a hearing aid for processing sound signals based on input of a user is described in DE 101 14 015, whereby the user classifies ambient sound signals as useful or interference signals. Useful signals will be highlighted, and interference signals or noise will be suppressed. However, manual interaction by the user of such a hearing aid is required, which may be cumbersome on the one hand and which may lead to wrong classification, i.e. not adequate for a specific situation, on the other hand. Also, as user of such hearing protection device may be workers, i.e. employees, there might be contradiction between needs of an employer of the user and needs of a user being an employee regarding the hearing protection device. For example, the employer has to ensure that the hearing protection device effectively protects the user's hearing in specific hearing situations, whereas the employee as user may wish to listen to specific sound desired on personal preferences. The latter could lead to ineffective set up—of a hearing protection device.

It is therefore a need to provide a hearing protection device taking different hearing situations into account while avoiding manual interaction and thereby minimizing the risk of inadequate hearing protection. Also, there is a need to prioritize between user's needs and other needs, for example, required by an authority for the set-up of a hearing protection device.

The present disclosure relates to a hearing protection device for protection in different hearing situations. The device comprises at least one ambient microphone, configured to convert surrounding sound into an electrical ambient signal and a sound reproduction unit for reproducing a sound based on the electrical ambient signal from the at least one ambient microphone. The sound reproduction unit comprises at least one loudspeaker for converting an electrical loudspeaker signal into corresponding sound. Such an amplifier may be advantageous because the amplified electrical loudspeaker signal provides greater freedom in level and may enhance the audibility of the loudspeaker signal for a user. A loudspeaker may include one or more electroacoustic transducers that convert electrical signals into sound. Some loudspeakers may include one or more of a magnet, a voice coil, a suspension and diaphragm structure, or a membrane. The device further comprises a controller operably coupled to the at least one ambient microphone and the sound reproduction unit. The controller comprises a plurality of predetermined profiles for specific hearing situations. The controller is configured to associate a predetermined profile with a specific hearing situation based on the electrical ambient signal from the at least one ambient microphone. The controller processes the ambient signal to the sound reproduction unit according to parameters of the predetermined profile to generate an electrical loudspeaker signal for the at least one loudspeaker. The sound reproduction unit optionally comprises an amplifier configured to amplify the electrical loudspeaker signal from the controller. Processing the signal to the sound reproduction unit typically includes analogue or digital signal processing. A controller may, for example, include a microprocessor, a microcontroller, an integrated circuit, a digital or analogue signal processor or the like. Other controllers are also conceivable. Furthermore, although a controller and an amplifier are described as different components of a hearing protection device, a controller may also include an amplifier, i. e. one component may provide the function of the controller and the amplifier at the same time. The advantage of such a hearing protection device is that it is set-up appropriately to a specific hearing situation surrounding the user of a hearing protection device. For example, a first specific hearing situation is taken into account and the frequency range and/or the level may be restricted for a user being in this hearing situation versus an unrestricted frequency range or level in another hearing situation different from the first hearing situation. By detecting a hearing situation and by setting up the hearing protection device accordingly, wrong set-up is avoided which may lead to hearing damage of the user on the one hand and to ineffective working condition not hearing relevant sound on the other hand. In other words, an automation of the hearing protection set-up is achieved thereby. Also, the hearing protection device according to the present disclosure provides an effective balance and/or prioritization between safety, work efficiency, user comfort and user needs when sound reproduction is working/optimized to present sound environment. Furthermore, misuse or unintentional wrong set-up is being minimized as the hearing protection device is being set-up according to the sound environment and both, the employer needs and the employee needs. This enables the user to be more in focus with a better comfort level, compared to other systems.

The present disclosure furthermore relates to a method of switching a hearing protection device according to the present disclosure in different hearing situations. The method comprises the steps of providing a hearing protection device according to the present disclosure, converting surrounding sound by at least one ambient microphone, into an electrical ambient signal, associating a predetermined profile with a specific hearing situation based on the electrical ambient signal from the at least one ambient microphone processing the electrical ambient signal to a sound reproduction unit of the hearing protection device by the controller according to parameters of a predetermined profile thereby generating an electrical loudspeaker signal to at least one loudspeaker of the hearing protection device, optionally an amplifier for amplifying the electrical loudspeaker signal. The controller may also include the function of an amplifier or the controller and the amplifier may be separate components. Such a method is advantageous because it provides for an easy and reliable way of switching a hearing protection device in different hearing situations. Also, an automated set up of the hearing device is thereby achieved.

The present disclosure moreover relates to a controller for a hearing protection device according to the present disclosure for protection in different hearing situations. The controller is operably couplable to at least one ambient microphone, and to a sound reproduction unit of a hearing protection device. The controller comprises a plurality of predetermined profiles for specific hearing situations. The controller is configured to associate a predetermined profile with a specific hearing situation. The controller is configured to process the electrical ambient signal to the sound reproduction unit of the hearing protection device according to parameters of the predetermined profile to generate an electrical loudspeaker signal for the at least one loudspeaker. As mentioned above, the controller may be a separate component of a hearing protection device or may be combined with other functions or components, e. g. with an amplifier. Examples of controllers may be a microprocessor, an integrated circuit or the like. The advantage of a hearing protection device with such a controller is that a hearing protection device is set-up appropriately to a specific hearing situation surrounding the user of a hearing protection device. By detecting a hearing situation and by setting up the hearing protection device accordingly, wrong set-up is avoided which may lead to hearing damage or safety risks of the user on the one hand and to ineffective working condition not hearing relevant sound on the other hand. Also, the controller according to the present disclosure provides an effective balance between safety, work efficiency and user comfort when sound reproduction is working/optimized to present sound environment. Furthermore, misuse or unintentional wrong set-up is being minimized as the hearing protection device is being set-up according to the sound environment and an automated set up is achieved with such a controller. Also, the user is more in focus, compared to other systems. Moreover, such a controller may be retrofitted to conventional hearing protection devices thereby enabling these to protect reliably and conveniently in different hearing situations.

Sound is understood as a particular auditory impression or a vibration that is typically propagating in form of audible waves of pressure through a gaseous, liquid or solid transmission medium.

Users in the context of the present disclosure are persons wearing a hearing protection device. Users may be employees and may wear the hearing protection device, for example, at work. Such work environment may be at an employer's facility, e. g. a factory or the like.

Hearing situations are understood to be a summation of sound (direct or reflected from e. g. walls) from different sources, origin and/or direction impacting on a user. Different hearing situations may differ e. g. in level/intensity, frequency content, directionality characteristics, origin or time of exposure. Also, different hearing situations are characterized as situations, in which a user has specific needs. For example, a user may need to hear specific sound such as a warning signal like a fire alarm or a signal horn of a vehicle or the like. On the other hand, a user in a specific hearing situation may not want or must not hear other specific sound, e. g. sound emissions of working machines, vehicles or other devices necessary for work, but not necessary to specifically listen to. Even more specifically, such sound emissions may cause negative impact on a user while not being necessary to be heard. This negative impact may include noise-induced hearing impairment or total loss, exhaustion, loss of work efficiency and speech intelligibility. The definition of a hearing situation is specifically intended to balance the priority between the user's awareness for safety, work efficiency and comfort based on the present and/or time statistics of the signal from an ambient microphone or a voice microphone. In some hearing situations, the focus on safety is related to the fidelity of the reproduced sound. In other hearing situations, the focus on work efficiency is related to the speech intelligibility of both the surrounding sound and the incoming sound from connected communication equipment. Hearing situations may also focus on comfort relating to fidelity of low level sound but attenuation of high level sound. Examples of different hearing situations may include patrolling, observation, conversation, comfort. Attenuation of surrounding sound may be relevant when incoming sound from the connected communication equipment or information sound from the hearing protection device is present.

Hearing protection is understood as a limiter of sound exposure which can be worn by a user being exposed to hazardous noise in order to prevent noise-induced hearing-loss.

A profile in the context of the present disclosure is a collection of parameters for setting up a hearing protection device. Typically, a profile is a predetermined profile which was set up before use of a hearing protection device and usually built on experiences prior to use. A profile may, for example, be modified in that one or more parameters of a predetermined profile may be changed. Also, it may be conceivable to set up new profiles based on current experiences and/or user input to form a predetermined profile. These parameters may include frequency range and response, amplification, attenuation, level or the like. The parameters may relate to frequency domain and/or time domain based characteristics. Devices or components for influencing such parameters may include equalizers, amplifiers, attenuators, compressors and expanders. Also, other transient characteristics such as attack/release times, i.e. the waiting time or delay after which a hearing protection device goes back to a previous stage before a specific sound impact happened may be influencing the parameters. A profile can also contain parameters of the hearing protection device characteristics such as allowed connected equipment and the parameters of them or software-related parameters such as menu structures for the configuration of the device or product. Specific profiles are set up for the above-mentioned specific hearing situations (patrolling, observation, conversation, comfort) with predefined or predetermined parameters for each of these profiles.

Sensors are devices, modules, machines or subsystems that detect events or changes of the sensor or in the surrounding of the sensor. As a response to these events or changes, sensors generate an analogue or digital electrical signal and may send this signal to other components of a system, e. g. a controller of a hearing protection device, to which the sensor is operably coupled in a wired or wireless way. Typically, sensors detect specific events or changes, for example sound such as voice sound, ambient sound or the like. Such sound sensors would be referred to as microphones. Furthermore, the sensor may also be an accelerometer which detects an acceleration the sensor and device is undergoing, respectively. As a result, a calculation of a movement incl. velocity, direction etc. may be possible.

The terms "coupled" or "connected" refer to elements or components being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a controller operably coupled to an amplifier may allow the controller to transmit signals using the amplifier).

In one embodiment, the parameters of the predetermined profile of the hearing protection device comprise frequency response, amplification/attenuation, transient characteristics and/or combinations thereof. The advantage of such a profile is that all necessary parameters for a specific hearing situation are contained in a particular profile so that switching the hearing protection unit accordingly is easy and fast.

In another embodiment, the controller of the hearing protection device further comprises at least one sensor for detecting conditions of or around the device. The sensor converts conditions of or around the device into an electrical sensor signal. These conditions may, for example, be movements of the device/user, temperature, vibration, angle, pressure the user of the device may be exposed to. The advantage of such a sensor is that the determination of which hearing situation a user of the hearing protection is in is easier as more data is provided to the hearing protection device. That is, not only ambient sound is taken into account for the determination, but also other parameters as detected by the sensor. Thus, there is a higher accuracy of determination of the specific hearing situation and achieving a better switching of the hearing protection device.

In certain embodiments, the at least one sensor of the hearing protection device comprises an acceleration sensor. The acceleration sensor converts acceleration to which the device is exposed into an electrical acceleration signal. As mentioned above, the advantage of a sensor is to provide higher accuracy of determination of the hearing situation, in particular, using an acceleration sensor to provides detailed data about movement and orientation of the hearing protection device, i. e. of the user wearing such a device. As this data can be taken into account for determination of the hearing situation, the accuracy of determination is even further increased.

In yet another embodiment, the hearing protection device further comprises at least one voice sensor, preferably a voice microphone. The voice sensor is operably coupled to the controller and is configured to generate an electrical voice signal based on a user's voice. In this embodiment, the hearing protection device further comprises a transmission unit for transmitting electrical voice signals and/or for receiving electrical voice signals transmitted from other devices. Such devices may be other hearing protection devices, machines, computers or the like. Preferably, the voice sensor in this embodiment is a voice microphone which converts voice sound into an electrical voice signal. Alternatively, the voice sensor may be a bone conductor, which is in direct contact with a user's skin bone and which receives vibrations corresponding to voice sound, which are converted by the voice sensor into an electrical voice signal. Typically, the electrical voice signals transmitted to and/or received from other devices in this embodiment are based on a user's voice. Also, such electrical voice signals may include artificial voices or so-called ghost voices, i. e. a voice command or other informative sounds, e. g. a beep as an alert or the like, from a device, e. g. the hearing protection device. Typically, the voice sensor, preferably the voice microphone, is positioned close to the mouth of a user such that there is sufficient capture of a voice signal by the voice sensor, preferably voice microphone. The voice sensor, preferably the voice microphone, may be spaced from other sensors, in particular spaced from the ambient microphone. Such a hearing device with a voice sensor and a transmission unit is beneficial because it allows the user of such a hearing protection device to have communication with other users or devices while still wearing the hearing protection device and over a certain distance. Such devices may be hearing protection devices (the one the user is wearing, other hearing protection devices of other users) as well as further devices, e. g. machines, vehicles or the like the user is working or which are in the surrounding of the user.

In certain embodiments, the controller of the hearing protection device is configured to adjust parameters of the hearing protection device such that the electrical voice signal from the voice sensor and/or the electrical voice signal as received by the transmission unit is prioritized. Prioritization of the electrical signal means setting parameters of the hearing protection device such that a voice communication is emphasized such that the user is better able to listen thereto. Such a controller is beneficial because due to the voice signal prioritization, the communication of the user of the hearing protection device with other users or devices is enhanced.

In a further embodiment, the hearing protection device according to the present disclosure further comprises a first and a second cup. Each cup comprises at least one loudspeaker and at least one ambient microphone. The hearing protection device further comprises a headband extending between the first and second cup. Cups may be formed of a rigid or semi-rigid material such as a plastic material, which in some cases, may be non-conductive, dielectric plastic. Typically, the cups are made of a thermoplastic material and exhibit a hollow shape. Cups may be obtained by vacuum forming, injection molding or the like. The cups may also comprise acoustic insulating material in order to provide a noise reduction. The cups may further comprise cushions, which may abut around the ears of a user and which may contribute to the capability to dampen or otherwise reduce ambient sound from an environment outside of the cups. Typically, cushions are formed of any compressible and/or expanding material, such as foam, gel, air filled in a hollow shape, or any other such suitable material. Cushions may be attached to the cups by using an adhesive, form fit, press fit, mechanical fasteners or the like. In some cases, cushions may also be formed integrally with the cups such that portions of the cups are rather rigid or semi-rigid, whereas other portions of the cups, i.e. forming the cushions, are rather soft. Typically, the loudspeaker is positioned in the hollow shape of the cup facing towards the user's ears such that the loudspeakers can emit sound towards the user's ears. Such a hearing protection device with a first and second cup is advantageous because the cups may provide a good fit with the user's ears and also provide for an encapsulation of components of the hearing protection device such as the microphones, loudspeakers or the controller. Also, cups may provide for a compact and robust design of the hearing protection device. Typically, a headband is made of steel wires and/or plastic components and exhibits a shape of an arc. Such a headband is advantageous because it provides for a reliable and easy to use means for adjusting the hearing protection device and thus, for providing a good fit to a user wearing such device.

In still a further embodiment, the hearing protection device comprises a boom extending from one of the first and second cups or earplugs (as described below) to the voice sensor, preferably voice microphone, Such a boom is advantageous as the voice sensor, preferably the voice microphone, may be held by the boom in a close distance to the user's mouth when speaking and thereby spaced from the ambient microphone.

In still another embodiment, the hearing protection device comprises an antenna extending from one of the cups or earplugs (as described below). An antenna typically transmits and/or receives electrical signals to and/or from other hearing protection devices, optionally also from other devices like machines, vehicles etc. Typically, an antenna may be operably coupled to the controller by wireless or wired connection, for example, using interconnect. An antenna is useful to improve the signal transmission, i. e. sending and receiving of electrical signals from or to the hearing protection device In one embodiment, the hearing protection device further comprises an input unit operably coupled to the controller, the at least one ambient microphone, and/or the sound reproduction unit of the device. Such input units are commonly known as the human machine interface. The input unit optionally comprises at least one button. The input unit may be used for setting up parameters of the reproduction unit, selecting a profile, transferring profile information into the controller and/or set up other components such as the sensor or microphone etc. The at least one button may allow for switching the input unit between certain stages, for example switched-on stage, switched off stage and/or different operation modes. Also, the software running on such a hearing protection device may be updated through such an input unit, wherein the new software is being transferred to the controller of the device through the input unit. Furthermore, the input unit may comprise a connector for digital communication with e. g. computers and/or other devices. Such an input unit provides for an easy and reliable way of modifying settings of the hearing device by a user or by configuring the hearing protection device by a computer. Also, an easy and efficient way of getting input of detailed user need is provided thereby. Using buttons is helpful for the user to change settings of the hearing protection device.

In certain embodiments, the input unit of the hearing protection device is attached to the device. Such an input unit is beneficial as it is readily reachable for the user of such a hearing protection device.

In certain embodiments, the input unit of the hearing protection device is separate from the device and connectable thereto, optionally wirelessly connectable. The input unit may be a separate stand-alone device or may be part of another device, e. g. a computer, a device or vehicle the user is operating, a smartphone or the like. Such separate input unit is beneficial as it may be better positionable for a user of such a hearing protection device, for example on other protective equipment worn by the user such as a jacket or the like. Using a wirelessly connectable input unit allows for more operational freedom of the user as no cable connection is needed between input unit and hearing protection device. This may further enhance the wearing comfort of the user.

In one embodiment, in the method of switching a hearing device, the controller is configured to associate the predetermined profile with parameters of the sound reproduction unit. The advantage of such a method for switching a hearing protection device is that a hearing protection device is set-up appropriately to a specific hearing situation surrounding the user of a hearing protection device. By detecting a hearing situation and by setting up the hearing protection device accordingly, wrong set-up is avoided which may lead to hearing damage of the user on the one hand and to ineffective working condition not hearing relevant sound on the other hand. Also, the hearing protection device according to the present disclosure provides an effective balance between safety, work efficiency and user comfort when sound reproduction is working/optimized to present sound environment. Furthermore, misuse or unintentional wrong set-up is being minimized as the hearing protection device is being set-up according to the sound environment. In other words, an automated set up of the hearing protection device is achieved. Also, the user is more in focus, compared to other systems.

In another embodiment, in the method according to the present disclosure the hearing protection device further comprises at least one sensor for detecting conditions of or around the device. The sensor converts conditions of or around the device into an electrical sensor signal. Optionally, the sensor is an acceleration sensor which converts acceleration to which the device is exposed into an electrical acceleration signal. The advantage of using sensors, optionally acceleration sensors is that the hearing protection device can be switched more accurately because such conditions of or around the user and the device, respectively, will be taken into account when switching the device.

In a further embodiment, the hearing protection device according to the present disclosure further comprises a first and a second earplug. Each earplug comprises at least one loudspeaker and at least one ambient microphone and optionally a headband extending between the first and second earplug. Earplugs may be formed of a rigid or semi-rigid material such as a plastic material, which in some cases, may be non-conductive, dielectric plastic. Typically, the earplugs are made of a thermoplastic material and exhibit a tube-like shape connecting the outside (with the sensor or microphone) and the inside of the earplug (with the loudspeaker). Earplugs may be obtained by vacuum forming, injection molding or the like. The earplugs may also comprise acoustic insulating material in order to provide a noise reduction. The earplugs may comprise further parts, layers or the like. For example, the earplug may comprise a noise-absorption layer surrounding a material which is not noise-absorbing as such. Earplugs may be inserted at least partially into the ear canal of the ears of a user, which may contribute to the capability to dampen or otherwise reduce ambient sound from an environment outside of the earplugs. Typically, the loudspeaker is positioned in within the earplug facing towards the user's ear canal such that the loudspeakers can emit sound towards the user's ear canal. Such a hearing protection device with a first and second earplug is advantageous because the earplugs may provide a good fit with the user's ears and also provide for an encapsulation of components of the hearing protection device such as the sensors or microphones, loudspeakers or the controller. Also, earplugs may provide for a compact and robust design of the hearing protection device.

The invention was described in various embodiments above. It is understood by a person skilled in the art, that one, several or all of the above-mentioned embodiments can be combined with each other.

The invention will now be described in more detail with reference to the following Figures exemplifying particular embodiments of the invention:

DETAILED DESCRIPTION OF FIGURES

Figure 1:
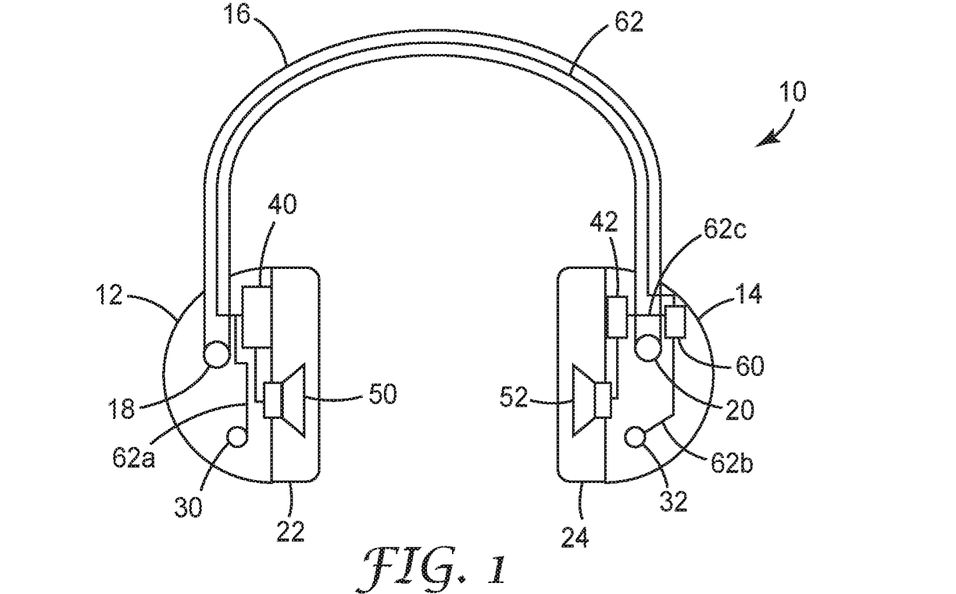
FIG. 1 is a cross-sectional front view of a hearing protection device according to one embodiment of the present disclosure.

FIG. 1 illustrates a hearing protection device 10 according to one embodiment of the present disclosure. The hearing protection device 10 comprises a first and a second cup 12, 14 connected by a headband 16. The cups 12, 14 are mechanically connected to the headband 16 via cup mounts 18, 20. Cup mounts 18, 20 may be arranged as pivot joints or hinges to allow for some movement of the cups 12, 14 relative to the headband 16, for example, to provide sufficient fit to the head of a user of the hearing protection device 10. The first and second cups 12, 14 comprise a first and a second ambient microphone 30, 32 mounted therein. The first and second ambient microphones 30, 32 are each connected to a controller 60 arranged in one cup 14. Microphone amplifiers 34, 36 are arranged between the first and second ambient microphone 30, 32 and the controller 60, which have been omitted in FIG. 1 for simplification (see FIG. 2 here). The controller 60 may also be arranged in the other cup 12 and/or two controllers may be arranged such that one controller is arranged in each of the cups 12, 14. The cups 12, 14 further comprise a first and a second loudspeaker 50, 52 each connected to a first and a second amplifier 40, 42 such that each of the loudspeakers 50, 52 is connected to an amplifier 40, 42. The loudspeakers 50, 52 and the amplifiers 40, 42 form the sound reproduction unit 38 (not shown here, see FIG. 2). The loudspeakers 50, 52 are to convert an electrical loudspeaker signal from the amplifiers 40, 42 into sound which a user wearing the hearing protection device (not shown here) can listen to. The first and the second amplifier 40, 42 are each connected to the controller 60 and are configured to generate and/or amplify an electrical loudspeaker signal for the loudspeakers 50, 52. As an alternative, only one amplifier supplying both loudspeakers 50, 52 may be arranged (not shown here). The headband 16 comprises a connection 62 for connecting the first amplifier 40 mounted in the first cup 12 to the controller 60 mounted in the second cup 14. Similarly, the connection 62 connects the first ambient microphone 30 mounted in the first cup 12 to the controller 60 arranged in the second cup 14. The connection 62 is arranged as a multi-channel connection or bus connection to allow for simultaneous transmission of several different electrical signals, e. g. an electrical ambient signal from the ambient sensor or microphone, or an electrical loudspeaker signal to the loudspeaker. In the embodiment shown in FIG. 1, the connection 62 provides for the general electrical connection between components in the first and second cup 12, 14. Further connections 62a, 62b, 62c are shown to provide for connection from the controller 60 in the second cup 14 to the ambient microphones 30, 32 being in the first or second cup 12, 14 as well as from the controller 60 to the amplifier 42 in the second cup 14. The first and the second cups 12, 14 further comprise a first and a second ear cushion 22, 24 such that one ear cushion 22, 24 is mounted to one cup 12, 14. The ear cushions 22, 24 provide for a soft and comfortable connection between the cups 12, 14 and the head, in particular the pinnas of the ears, of a user of the hearing protection device 10. The cushions 22, 24 further provide for a reasonable seal between head and the cups 12, 14 such that noise impacting on the user cannot reach or only reach to a low degree the ear drums of the user.

Figure 2:
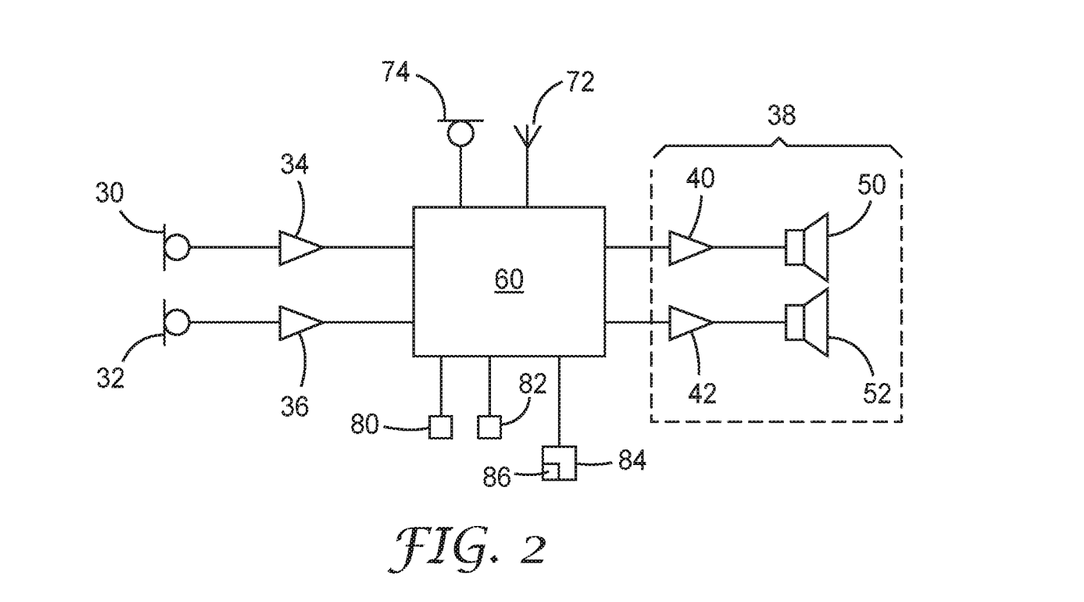
FIG. 2 is a block diagram illustration of the hearing protection device according to one embodiment of the present disclosure.

FIG. 2 schematically shows a block diagram of the hearing protection device 10. FIG. 2 shows a first and a second ambient microphone 30, 32 convert surrounding sound into electrical ambient signals. The microphones 30, 32 are connected to a first and a second microphone amplifier 34, 36 for amplifying an electrical ambient signal coming from the microphones 30, 32. The microphone amplifiers 34, 36 are in turn connected to the controller 60. The controller 60 processes the incoming electrical ambient signals from the microphones 30, 32 and microphone amplifiers 34, 36, respectively, such that the controller 60 determined the hearing situation the user of such a hearing protection device 10 may be in. The controller 60 is connected to a sound reproduction unit 38 comprising a first and a second amplifier 40, 42 which receive a processed electrical ambient signal from the controller 60. The sound reproduction unit 38 further comprises a first and second loudspeaker 50, 52. The amplifiers 40, 42 amplify the electrical loudspeaker signals coming from the controller 60 such that these can be converted into sound at the loudspeakers 50, 52 connected to the amplifiers 40, 42. The electrical loudspeaker signal going to the amplifiers 40, 42 and the loudspeakers 50, 52 is processed based on a profile associated by the controller 60 with a specific hearing situation determined by the controller 60. The controller 60 is also connected to a voice microphone 74 and to an antenna 72. The voice microphone 74 is configured to convert a voice sound into an electrical voice signal to be transmitted to the controller 60. The controller 60 transmits such an electrical voice signal coming from the voice sensor or microphone 74 via the antenna 72 to other communication equipment such that a voice communication between the user of the hearing protection device and other people or products such as other hearing protection devices, machines, vehicles, computer or the like is enabled. The controller 60 further comprises a first and a second sensor 80, 82 for detecting conditions of or around the hearing protection device 10 and the user of such device 10, respectively. Such conditions may, for example, be movements, acceleration, orientation, vibration, light exposure, temperature, vibrations or the like. For example, the sensor 80 may be an accelerometer for detecting acceleration of the device 10 and the user wearing it, respectively. The sensor 82 may, for example, be a temperature sensor to detect the ambient temperature which is impacting onto the device 10 and the user, respectively. FIG. 2 further shows an input unit 84 connected to the controller 60 for allowing to set up parameters of the controller 60 or for transferring data to the controller 60 via a human machine interface, for example, preferences of the user, preferences of the employer, environmental data, regulations and profile data. The input unit 84 comprises at least one button 86, which may be used for switching the input unit 84.

Figure 3:
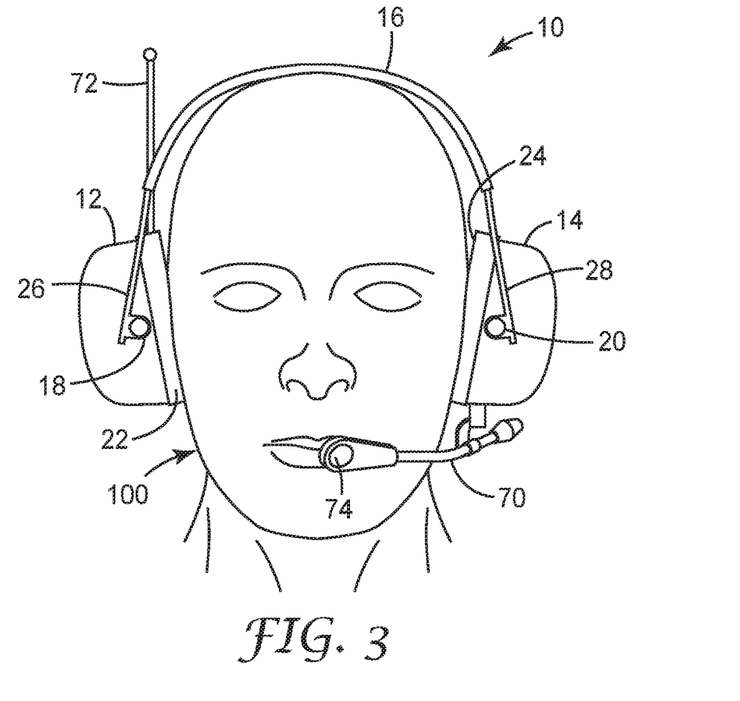
FIG. 3 is a front view of a user wearing a hearing protection device according to another embodiment of the present disclosure.

FIG. 3 shows a user 100 wearing a hearing protection 10 similar to the hearing protection 10 as shown in FIG. 1. The hearing protection device 10 comprises a first and a second cup 12, 14 mounted to a headband 16 via mounts 18, 20. Mounts 18, 20 are connected to headband mount 26, 28 formed by a section of the headband 16. An antenna 72 extends from one of the cups 12 for allowing improvement of a signal transmission, for example of an electrical voice signal from or to the hearing device 10. FIG. 3 further shows a microphone boom 70 extending from one of the cups 14 towards the voice microphone 74 such that the voice microphone 74 is held in a position close to the user's mouth. A good sound transfer of the mouth to the voice microphone 74 when the user is speaking is thereby achieved. As can be seen in FIG. 3, ear cushions 22, 24 are arranged between the cups 12, 14 and the user's head such that a good wearing comfort of the hearing protection device is achieved.

Figure 4:
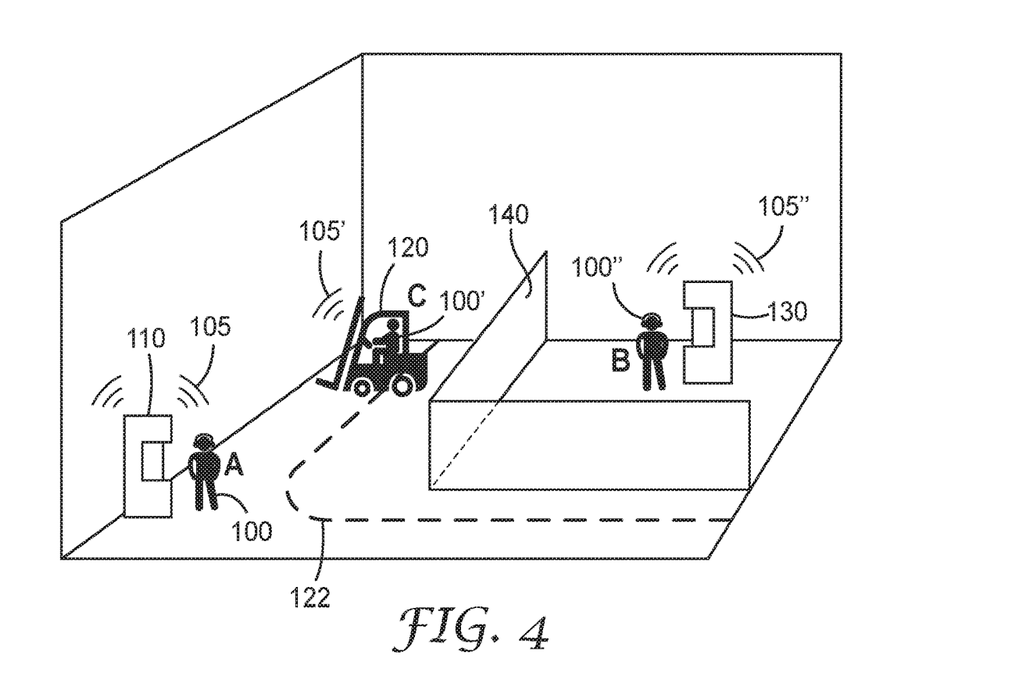
FIG. 4 is a perspective view of users wearing a hearing protection device according to the present disclosure where different users are in different hearing situations.

FIG. 4 shows exemplary hearing situations A, B, C. In these, the user 100, 100', 100" is exposed to sound in different ways. Thus, the need for hearing protection may be different for the user 100, 100', 100" in these different hearing situations A, B, C. In situation A, the user 100 wearing a hearing protection device is exposed to sound of a machine 110 as indicated with 105. The user 100 may also be exposed with other sound, for example coming from sound sources of another hearing situation, i. e. sound sources at B, C indicated by 105', 105". The user 100' in hearing situation B is exposed to sound of a machine 130 indicated by 105". The user 100' may also be exposed to sound from other sound sources of hearing situations, i.e. sound sources at A, C as indicated by 105, 105". The user 100" in hearing situation C is exposed to sound of a forklift 120 indicated by 105'. The user 100" may also be exposed to sound from other sound sources at hearing situations, i.e. sound sources at A, B as indicated by 105, 105'.

These different hearing situations A, B, C will now be described in more detail. As mentioned above, the user 100 in hearing situation A may be exposed to different sound. Also, the user 100 may be in danger to be hit by the forklift 120 from hearing situation C when it is driving along driveway 122. As hearing situation A indicated in FIG. 4 is in a rather open space, user 100 may also move around to a higher extent compared to the other hearing situations, in particular compared to hearing situation B, where the user 100" is in an encapsulated environment. Thus, there is a need for the user 100 in hearing situation A to hear sound like an alarm sent off from the signal horn of the forklift 120 while crossing the walk way of the user 100. Although this sound may add up to the overall sound impacting and have negative effects on the user 100, it is very important for the user 100 to hear sound such as, for example, the alarm of a driving or crossing forklift 120. This leads to a prioritization in the signal processing of the hearing protection device, and it is not overall important to have an ideal sound attenuation of surrounding sound for user 100. This may compromise the best possible comfort of the user 100 to some extent, but is nevertheless important for user 100 in order to move safely in the respective environment.

FIG. 4 further shows another hearing situation B, in which the user 100" of a hearing device is encapsulated by walls 140 such that the forklift 120 of hearing situation C may not come close to the user 100". On the one hand, there may thus not be a need for the user 100' of the forklift 120 to send an alarm off towards the user 100" and for the user 100" to hear such alarm sound, respectively. On the other hand, in particular if the walls 140 have a sound absorption function, the user 100" may not or only to a little extent be able to hear such an alarm sound from the forklift 120 at all. The user 100" is, of course, be exposed to sound generated by machine 130 the user 100" is working at. This sound is indicated by 105", which impacts onto the user 100". This sound may also impact on the other users 100, 100' in the other hearing situations A, B. As the user 100" is in an encapsulated environment, i.e. no forklift 120 or the like is crossing, the hearing protection device—as mentioned above—may not need to take such external sound into account. Thus, there are less restrictions on the signal processing of the sound to the user 100" in this specific environment or hearing situation B, respectively, to move safely in that environment.

As further shown in FIG. 4, the user 100' in hearing situation C may have different sound impacting on the user 100' and also different needs. The user 100' is driving a forklift 120, as mentioned above, along driveway 122. Thus, sound emissions from the forklift 120 may impact on the user 100' as indicated by 105'. As the forklift 120 is moving—similarly to user 100 in hearing situation A—in a rather open space, the user 100' may also be exposed to other sound emissions, e. g. coming from machine 110 in hearing situation A. So, the hearing protection device (not shown here for simplification) worn by the user 100' should not only take the sound emissions from the fork lift 120 into account, but also the other sound emission, e. g. from machine 110, or e.g. speech communication from A or B when setting up or switching parameters of the hearing protection device.

Figure 5:
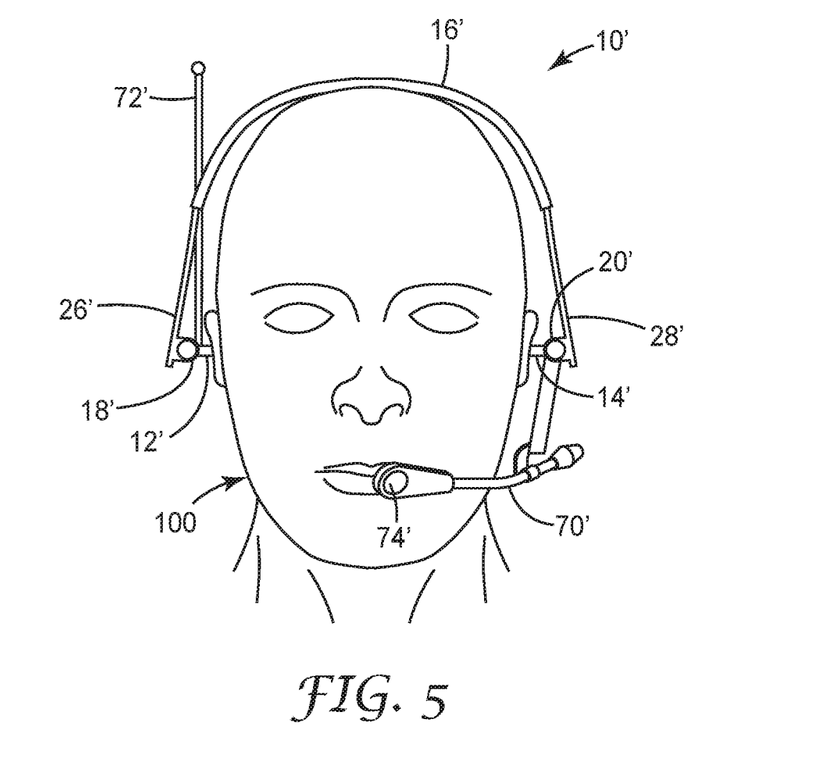
FIG. 5 is a front view of a user wearing a hearing protection device according to another embodiment of the present disclosure.

FIG. 5 shows a user 100 wearing a hearing protection 10' similar to the hearing protection 10 as shown in FIGS. 1 and 3. The hearing protection device 10' comprises—different to that in FIGS. 1 and 3—a first and a second earplug 12', 14' mounted to a headband 16' via mounts 18', 20'. Mounts 18', 20' are connected to headband mount 26', 28' formed by a section of the headband 16'. An antenna 72' extends from one of the earplugs 12' for allowing improvement of a signal transmission, for example of an electrical voice signal from or to the hearing device 10'. FIG. 5 further shows a microphone boom 70' extending from one of the earplugs 14' towards the voice microphone 74' such that the voice microphone 74' is held in a position close to the user's mouth. A good sound transfer of the mouth to the voice microphone 74' when the user is speaking is thereby achieved. Different to FIGS. 1 and 3, as can be seen in FIG. 5, no ear cushions 22, 24 are arranged between the earplugs 12', 14' and the user's head.

The invention claimed is:

1. A hearing protection device for protection in different hearing situations, the device comprises:
   a. at least one ambient microphone, configured to convert surrounding sound into an electrical ambient signal, a sensor configured to detect a condition around the hearing protection device;
   b. a sound reproduction unit for reproducing sound based on the electrical ambient signal from the at least one ambient microphone, the unit comprising at least one loudspeaker for converting the electrical loudspeaker signal into corresponding sound; and
   c. a controller operably coupled to the at least one ambient microphone and the sound reproduction unit, the controller comprises a plurality of predetermined profiles for specific hearing situations,
   wherein the controller is configured to:
      determine a specific hearing situation based on the electrical ambient signal from the at least one ambient microphone and the detected condition;
      associate a predetermined profile with the specific hearing situation, and
      automatically, based on the determination and association, process the electrical ambient signal to the sound reproduction unit according to parameters of the predetermined profile to generate an electrical loudspeaker signal for the at least one loudspeaker,
   wherein the sound reproduction unit comprises an amplifier for amplifying the electrical loudspeaker signal from the controller, and
   wherein the parameters of the predetermined profile comprise frequency response, amplification/attenuation, transient characteristics and/or combinations thereof for the specific hearing situation.

2. The device according to claim 1, wherein the sensor comprises an acceleration sensor, wherein the acceleration sensor converts acceleration to which the device is exposed into an electrical acceleration signal.

3. The device according to claim 1, further comprising an input unit operably coupled to the controller, the at least one ambient microphone, and/or the sound reproduction unit of the device.

4. The device according to claim 3, wherein the input unit is attached to the device.

5. The device according to claim 3, wherein the input unit comprises an input device physically distinct from the device, but operably couplable to the device.

6. The device according to claim 1, further comprising at least one voice sensor operably coupled to the controller and configured to generate an electrical voice signal based on a user's voice and a transmission unit for transmitting electrical voice signals and/or for receiving electrical voice signals transmitted from other devices.

7. The device according to claim 6, wherein the controller is configured to adjust parameters of the hearing protection device such that the electrical voice signal from the voice sensor and/or the electrical voice signal as received by the transmission unit is prioritized over the electrical ambient signal.

8. The device according to claim 1, further comprising a first and a second cup, each cup comprising at least one loudspeaker, at least one ambient microphone and a headband extending between the first and second cup.

9. The device according to claim 1, further comprising a first and second earplug, each earplug comprises at least one loudspeaker and at least one ambient microphone.

10. A method of switching a hearing protection device according to claim 1 in different hearing situations, the method comprising the steps of
    a. providing a hearing protection device according to claim 1,
    b. converting surrounding sound by at least one ambient microphone, into an electrical ambient signal,
    c. a determining a specific hearing situation based on the electrical ambient signal from the at least one ambient microphone,
    d. associating a predetermined profile with the specific hearing situation,
    e. processing the electrical ambient signal to a sound reproduction unit of the hearing protection device by the controller according to parameters of a predetermined profile thereby generating an electrical signal to at least one loudspeaker of the hearing protection device, and
    wherein the parameters of the predetermined profile comprise a frequency response, an amplification/attenuation, a transient characteristic and/or combinations thereof for the specific hearing situation.

11. The method according to claim 10 wherein the controller is configured to associate the predetermined profile with parameters of the sound reproduction unit.

12. The method according to claim 10, wherein the hearing protection device further comprises at least one sensor for detecting conditions of or around the device, wherein the sensor converts conditions of or around the device into an electrical sensor signal, which converts acceleration to which the device is exposed into an electrical acceleration signal.

13. A controller for a hearing protection device according to claim 1 for protection in different hearing situations, the controller being operably couplable to at least one ambient microphone, a sensor, and to a sound reproduction unit of a hearing protection device, the controller comprises a plurality of predetermined profiles for specific hearing situations,
    wherein the controller is configured to:
       receive a sensor signal indicative of a condition of or around the hearing protection device;
       determine a specific hearing situation based on the electrical ambient signal from the at least one ambient microphone and the received sensor signal;
       associate a predetermined profile with the specific hearing situation,
       process the electrical ambient signal to the sound reproduction unit of the hearing protection device according to parameters of the predetermined profile to generate an electrical loudspeaker signal for the at least one loudspeaker; and
       wherein the parameters of the predetermined profile comprise frequency response, amplification/attenuation, transient characteristics and/or combinations thereof for the specific hearing situation.

14. The device of claim 3, wherein the input unit comprises at least one button.

15. The device of claim 3, wherein the input unit is wirelessly coupled to the controller, the at least one ambient microphone, and/or the sound reproduction unit of the device.

16. The device of claim 6, wherein the voice sensor comprises a voice microphone.

17. The method of claim 12, wherein the sensor is an acceleration sensor.

18. The device of claim 1, wherein the predetermined profile is a second predetermined profile and wherein automatically, based on the determination and association, process the electrical ambient signal to the sound reproduction unit according to parameters of the predetermined profile to generate an electrical loudspeaker signal for the at least one loudspeaker comprises switching from a first predetermined profile to the second predetermined profile.

19. The device according to claim 1, wherein the sensor is configured to detect a movement of the device, an ambient temperature, a vibration, an angle of the device, or a pressure the device is exposed to.

20. The device according to claim 18, wherein the second predetermined profile comprises an unrestricted frequency range, and wherein the first predetermined profile comprises a restricted frequency range.

\* \* \* \* \*

UNITED STATES PATENT AND TRADEMARK OFFICE
CERTIFICATE OF CORRECTION

Page 1 of 1

PATENT NO. : 12,193,914 B2
APPLICATION NO. : 17/756370
DATED : January 14, 2025
INVENTOR(S) : Oscar KÅrekull et al.

It is certified that error appears in the above-identified patent and that said Letters Patent is hereby corrected as shown below:

In the Claims

<u>Column 14</u>
Line 11 (approx.), In Claim 10, delete "a", before "determining".

Signed and Sealed this
Seventeenth Day of June, 2025

Coke Morgan Stewart
*Acting Director of the United States Patent and Trademark Office*